United States Patent [19]
> Stapp

[11] 4,003,923
[45] Jan. 18, 1977

[54] PREPARATION OF QUINONES
[75] Inventor: Paul R. Stapp, Bartlesville, Okla.
[73] Assignee: Phillips Petroleum Company, Bartlesville, Okla.
[22] Filed: Feb. 19, 1975
[21] Appl. No.: 551,128
[52] U.S. Cl. .............................. 260/369; 260/370; 260/385; 260/365; 260/396 R; 260/590 R
[51] Int. Cl.² ................ C07C 49/68; C07C 49/62
[58] Field of Search ...... 260/385, 369, 370, 396 R, 260/365, 590 R

[56] References Cited
UNITED STATES PATENTS

| | | | |
|---|---|---|---|
| 3,505,361 | 4/1970 | Greco | 260/385 |
| 3,642,838 | 2/1972 | Calderazzo | 260/385 |
| 3,723,510 | 3/1923 | Ono et al. | 260/497 R |
| 3,855,252 | 12/1974 | Robinson et al. | 260/385 |

OTHER PUBLICATIONS

Digurov et al., Chemical Abstracts 74 (1971), No. 64118e (abstract of Russian Patent 280469).

*Primary Examiner*—Arthur P. Demers

[57] ABSTRACT

Quinones are prepared by the catalytic oxidation of aromatic compounds selected from the group consisting of acenaphthene, fused ring structures having 3 to 5 six-membered rings and sulfonic acid derivatives thereof in the liquid phase in carboxylic acid medium in the presence of a catalyst system consisting of a copper compound and an alkali metal compound.

5 Claims, No Drawings

PREPARATION OF QUINONES

This invention relates to the production of quinones.

Quinones are important raw materials for dyestuffs and as intermediates. Anthraquinone, one of the more important quinones, is prepared in large quantities, in general, by two processes. One involves the reaction of phthalic anhydride and benzene by a Friedel-Crafts reaction to form benzoylbenzoic acid which is then ring closed to form the anthraquinone. The process is expensive since it involves several steps. Another process is the vapor phase catalytic oxidation of anthracene. This process requires relatively pure anthracene.

Other processes have been proposed. One such process involves the oxidation of anthracene with molecular oxygen in the liquid phase in the presence of catalysts or of oxygen carriers such as the nitrites or oxides of nitrogen. In general, this process has not been as economical as those starting with phthalic anhydride or the vapor phase catalytic oxidation of anthracene.

Another process involves the oxidation of anthracene with molecular oxygen at elevated temperatures and pressures in a carboxylic acid medium. No catalyst is required, however, the process is relatively expensive due to the requirement for high pressure reaction apparatus.

It is an object of this invention to provide a process for the production of quinones.

Other objects, aspects and advantages of this invention will be readily apparent to those skilled in the art from the reading of the following disclosure.

In accordance with the present invention there is provided a process for the production of quinones from the corresponding aromatic hydrocarbon which comprises reacting under reaction conditions an aromatic compound selected from the group consisting of acenaphthene, fused ring compounds having from 14 to 22 carbon atoms per molecule and containing from 3 to 5 six-membered carbocyclic rings, and mono-sulfonic acid derivatives thereof, with oxygen in the liquid phase in carboxylic acid medium in the presence of a catalytic amount of a catalyst system consisting of a copper compound and an alkali metal compound.

An important advantage of the present invention is that reaction conditions are relatively mild as compared to the prior art. The reaction is carried out at a temperature in the range of from 30° to about 200° C, preferably from about 100° to about 150° C.

The reaction is carried out under a pressure of from 0.1 to about 750 psig, preferably from about 5 to about 200 psig, of oxygen above autogenous pressure at the temperature employed.

The reaction time depends generally on the temperature, oxygen pressure and the activity of the catalyst employed. In general, it is desired to carry out the reaction to essentially complete conversion of the starting aromatic compound to the quinone. Usually, this can be determined by observation that the reaction mixture no longer takes up oxygen. Depending upon reaction conditions then, the reaction time will range from about 0.1 to about 24 hours, although longer reaction times may be required in some instances.

Examples of aromatic compounds which can be used according to the process of this invention to produce the corresponding quinone include: acenaphthene, anthracene, phenanthrene, naphthacene, pentacene, picene, 1-anthracenesulfonic acid, 2-naphthacenesulfonic acid, 2-chrysenesulfonic acid, 1-pentacenesulfonic acid and the like.

Examples of quinones which can be produced from the above starting compounds include: acenaphthenequinone, 9,10-anthraquinone, 9,10-phenanthrenequinone, 5,12-naphthacenequinone, 5,6-chrysenequinone, 6,13-pentacenequinone, 5,6-picenequinone, 9,10-anthraquinone-1-sulfonic acid, 5,12-naphthacenequinone-2-sulfonic acid, 5,6-chrysenequinone-2-sulfonic acid, 6,13-pentacenequinone-1-sulfonic acid and the like.

The reaction of the present invention is carried out in the liquid phase in carboxylic acid medium. The carboxylic acids suitable for use as the reaction medium are selected from the group consisting of saturated aliphatic carboxylic acids having from 2 to 10 carbon atoms per molecule. It is preferred that the carboxylic acid employed be normally liquid. It must, of course, be liquid under the reaction conditions employed.

Examples of suitable carboxylic acids include: acetic acid, propanoic acid, butanoic acid, pentanoic acid, hexanoic acid, 2-ethylhexanoic acid, and the like and mixtures thereof.

It is presently preferred that the process be carried out in the absence of water. Optionally, a carboxylic acid anhydride can be employed in admixture with the carboxylic acid reaction medium to remove any water which may be produced during the course of the reaction. Where such anhydride is used, it is preferred that it correspond to the carboxylic acid employed.

In a presently preferred embodiment the reaction medium is acetic acid, due to the ready availability of that acid. In a more preferred embodiment, the reaction medium is a mixture of acetic acid and acetic anhydride.

The reaction of the instant invention is an oxidation reaction and as such is carried out in the presence of free oxygen. The amount of oxygen present is not believed to be critical though it is recognized that an undesirably slow reaction will result if the concentration of oxygen is very low. Essentially pure oxygen can be employed as well as mixtures of oxygen with inert gases or air can be employed as the source of free oxygen for the instant reaction. Due care should be exercised when adding oxygen to the reaction mixtures of the instant invention to avoid the possible build-up of explosive concentrations of oxygen. In addition, the reaction of the instant invention is an exothermic reaction. Because of these considerations, it is desirable to add the oxygen incrementally or continuously during the reaction to avoid the explosive range of oxygen concentration and to allow better control of the temperature of the reaction. A reaction vessel with efficient mixing means is also desirable in order to avoid build-up of dangerous concentrations of free oxygen.

The oxidation of the above described aromatic compounds to the quinones in the presence of the above described carboxylic acid medium is conducted in the presence of a catalyst system consisting of a copper compound and an alkali metal compound. The copper compound can be in the cuprous or cupric form, or mixtures of these can be used. Suitable copper compounds include the carboxylates, halides, oxides, carbonates and the like.

Examples of suitable copper compounds for use as catalysts in the present invention include: copper (II) acetate, copper (I) bromide, copper (II) bromide, copper (II) benzoate, copper (II) butanoate, copper (I)

chloride, copper (II) chloride, copper (II) dodecanoate, copper (I) oxide, copper (II) oxide, copper (II) salicylate, copper (I) iodide, copper (I) carbonate and the like.

The amount of copper compound employed as catalyst in the process of this invention is in the range of about 0.1 to about 50 mole percent based upon the starting aromatic compound. It is presently preferred that the copper compound catalyst be present in the reaction mixture in an amount ranging from about 1 to about 25 mole percent of the starting aromatic compound.

The second component of the catalyst system is an alkali metal compound such as a halide, carboxylate, oxide or the like. Of the alkali metal salts, the lithium salts are especially preferred. The alkali metal salt is employed in an amount ranging from 0.1 to 2 molar, preferably from about 0.3 to about 1.5 molar, based upon the carboxylic acid reaction medium.

Examples of suitable alkali metal salts which can be employed as the catalyst adjuvant include: lithium chloride, lithium bromide, lithium iodide, lithium acetate, lithium benzoate, lithium oxide, lithium octadecanoate, sodium chloride, sodium bromide, sodium acetate, potassium chloride, potassium acetate, potassium benzoate, rubidium chloride, rubidium bromide, rubidium acetate, cesium chloride, cesium acetate, cesium oxide, and the like.

The quinones, which are produced according to the process of this invention, can be recovered from the reaction mixture by mixing the reaction mixture with water and recovering the precipitated quinone therefrom. Alternatively, the carboxylic acid diluent can be distilled from the reaction mixture, and the quinone extracted from the catalyst residue by an organic solvent, such as ether, from which the quinone can be recovered by distilling away the ether. Further purification of the quinone can, of course, be accomplished by conventional procedures, such as recrystallization from suitable solvents.

As indicated above, it is desirable to carry out the reaction to essentially complete conversion of the starting aromatic compound. One reason for this desideratum is that if such complete conversion is not attained, there are formed intermediates which may be difficult to separate from the desired quinone and thus complicate separation procedures in the reaction mixture work-up.

The quinones produced according to the process of this invention are known generally to have utility as intermediates in the preparation of dyes. Quinones are also used in photographic compositions containing vinyl polymers and as intermediates in the preparation of compounds used in chemiluminescent systems. The sulfonic acid-substituted quinones can be employed as weak oxidizing agents.

The following examples illustrate the invention.

EXAMPLE I

A 250 ml Fisher-Porter aerosol compatibility bottle equipped with a magnetic stirrer was employed as the reactor for a run carried out according to this invention. The reactor was charged with 3.2 grams (37.5 mmol) of lithium bromide, 4.8 grams (24 mmol) of cupric acetate monohydrate, 18.8 grams (100 mmol) of anthracene (Practical Grade), 75 ml of acetic acid and 25 ml of acetic anhydride. The reactor was pressured with oxygen to 30 psig, placed in an oil bath and heated to 140° C. About 1 hour was required to reach the reaction temperature, and the reaction was conducted for an additional 8 hours at this temperature. During the reaction period, the reactor was pressured to 60–80 psig with oxygen intermittently and during the last 45 minutes of the reaction period, there was observed essentially no decrease in oxygen pressure, which indicated that the reaction had apparently gone to completion. At the end of the reaction period, the reactor was vented, and the reaction mixture mixed with 500 ml of water and stirred while boiling the mixture for 2 hours. The mixture was then diluted with water to replace that lost during the boiling operation and the mixture was allowed to cool to room temperature. The solid precipitate which had formed was collected, washed with water and dried in the air. This material was then recrystallized from benzene to give 13.2 grams of product with a melting point of 278°–282° C. Additional product was obtained by crystallizing material from the mother liquor and there was obtained 5.9 grams with a melting point of 275°–280° C by this operation. The above materials were analyzed by infrared spectroscopy and were identified as 9,10-anthraquinone. The yield of 9,10-anthraquinone was thus 19.1 grams for a 91.8 percent yield based on the starting anthracene.

The results of this run demonstrate that the catalyst system of the instant invention provided an excellent yield of 9,10-anthraquinone by oxidation of anthracene.

EXAMPLE II

A run was carried out employing the same apparatus as that used in Example I above. In this run, the reactor was charged with 4.8 grams (24 mmol) of cupric acetate monohydrate and 18.8 grams (100 mmol) of anthracene, 75 ml of acetic acid, and 25 ml of acetic anhydride. The reactor was placed in an oil bath, pressured to 30 psig with oxygen and heated to 140° C for 7.8 hours. The reactor was pressured to about 60 psig with oxygen at intervals of about 30 minutes. There was apparently very little oxygen consumption during the reaction period. At the end of the reaction period, the mixture was poured into 400 ml of water, stirred for 2 hours and then filtered. The recovered solids were washed thoroughly with water and then dried in air to provide 16.9 grams of reaction product. An infrared spectrum of the product was essentially identical with that of the anthracene starting material which indicated that little, if any, oxidation had occurred during the reaction period. This result demonstrates that a catalyst system comprising a copper compound but without the alkali metal compound gives a very slow oxidation of anthracene under the conditions employed.

Reasonable variations and modifications, which will be apparent to those skilled in the art, can be made in this invention without departing from the spirit and scope thereof.

What is claimed is:

1. A process for the production of quinones which comprises reacting an aromatic compound selected from the group consisting of acenaphthene, fused ring compounds having from 14 to 22 carbon atoms per molecule and containing from 3 to 5 six-membered carbocyclic rings, and mono-sulfonic acid derivatives thereof, with oxygen in the liquid phase in a carboxylic acid medium in the presence of a catalyst system consisting of a mixture of a copper compound and an alkali metal compound, wherein said copper compound is selected from the group consisting of the carboxylates, halides, oxides and carbonates thereof, and wherein said alkali metal compound is selected from the group consisting of the halides, carboxylates and oxides thereof, said reaction being carried out at a temperature in the range of from 30° to about 200° C and a pressure in the range of from 0.1 to about 750 psig of oxygen above autogenous pressure at the temperature employed, wherein said copper compound is present in an amount ranging from about 0.1 to about 50 mole percent based on said aromatic compound and said alkali metal compound is present in an amount ranging from 0.1 to 2 molar based on said carboxylic acid medium.

2. The process of claim 1 wherein said medium comprises at least one saturated aliphatic carboxylic acid having from 2 to 10 carbon atoms per molecule.

3. The process of claim 1 wherein there is additionally present in said medium a carboxylic acid anhydride.

4. The process of claim 1 wherein said copper compound is present in an amount ranging from about 1 to about 25 mole percent of said aromatic compound and said alkali metal compound is present in an amount ranging from 0.3 to 1.5 molar based on said medium.

5. The process of claim 1 wherein said aromatic compound is anthracene, said copper compound is cupric acetate, said alkali metal compound is lithium bromide and said quinone is 9,10-anthraquinone.

* * * * *